United States Patent [19]

Haag et al.

[11] Patent Number: 4,508,836
[45] Date of Patent: Apr. 2, 1985

[54] CATALYTIC CONVERSION PROCESS FOR AROMATIC FEEDSTOCKS WITH HYDROGEN REGENERATION OF COKE-SELECTIVATED ZEOLITE CATALYST

[75] Inventors: Werner O. Haag, Lawrenceville; David H. Olson, Pennington; Paul G. Rodewald, Rocky Hill, all of N.J.

[73] Assignee: Mobil Oil Corporation, New York, N.Y.

[21] Appl. No.: 472,822

[22] Filed: Mar. 7, 1983

[51] Int. Cl.³ .................. B01J 29/38; C07C 2/66; C07C 5/22
[52] U.S. Cl. .................. 502/53; 585/466; 585/467; 585/471; 585/475; 585/481
[58] Field of Search .............. 252/411 R, 437, 455 Z; 585/466, 467, 471, 475, 481; 502/53

[56] References Cited

U.S. PATENT DOCUMENTS

| | | | |
|---|---|---|---|
| 3,412,013 | 11/1968 | Bowles | 208/120 |
| 4,001,346 | 1/1977 | Chu | 585/467 |
| 4,086,287 | 4/1978 | Kaeding et al. | 585/466 |
| 4,088,706 | 5/1978 | Kaeding | 585/412 |
| 4,117,026 | 9/1978 | Haag et al. | 585/475 |
| 4,128,592 | 12/1978 | Kaeding | 585/467 |
| 4,358,395 | 11/1982 | Haag et al. | 252/411 R |

*Primary Examiner*—P. E. Konopka
*Attorney, Agent, or Firm*—Alexander J. McKillop; Michael G. Gilman; Dennis P. Santini

[57] ABSTRACT

In the process of converting an aromatic feedstock to an alkyl-substituted mono-nuclear aromatic product by contacting the feedstock with a coke-selectivated ZSM-5 type catalyst at elevated temperature under conversion process coking conditions to produce said alkyl-1-substituted mononuclear aromatic product selectively, the improvement which comprises:

regenerating the process coked catalyst in contact with a non-oxidizing atmosphere comprising an effective amount of hydrogen at a temperature of about 800° F. to 1200° F. to restore activity of the catalyst while retaining selectivity. Advantageously, the conversion involves alkylation, disproportionation and/or isomerization to produce at least one lower alkyl or dialkyl benzene product.

17 Claims, 2 Drawing Figures

TIME ON STREAM (DAYS)

CATALYTIC CONVERSION PROCESS FOR AROMATIC FEEDSTOCKS WITH HYDROGEN REGENERATION OF COKE-SELECTIVATED ZEOLITE CATALYST

REFERENCE TO RELATED APPLICATIONS

This application is a continuation-in-part of application Ser. No. 402,391 filed July 27, 1982; now abandoned which is a continuation of application Ser. No. 941,606 filed Sept. 11, 1978, now U.S. Pat. No. 4,358,395.

BACKGROUND OF THE INVENTION

1. Field of the Invention

This invention relates to an improved method for regeneration of coke-selectivated ZSM-5 type crystalline aluminosilicate zeolite catalyst by treatment with hydrogen at elevated temperature.

2. The Prior Art

It has heretofore been known to employ coke-selectivated catalysts comprising a crystalline aluminosilicate zeolite having a silica to alumina mole ratio of at least about 12 and a constraint index between about 1 and about 12 for conversion of various organic compounds involving reactions such as alkylation, disproportionation, isomerization, cracking, polymerization, aromatization, etc. These catalysts have been found to be particularly useful in selective processes, such as selective toluene disproportionation and aromatics alkylation with olefins; as disclosed in U.S. Pat. No. 4,128,592 (Kaeding). The coke-selectivated catalysts so employed slowly deactivate with time on stream ultimately making regeneration thereof necessary.

Regeneration has heretofore been carried out by contacting the aged catalyst at an elevated temperature with an oxygen-containing atmosphere, e.g., air, to effect removal of coke therefrom. Such procedure has served to restore the activity of the catalyst but has resulted in very substantial reduction in selectivity of the catalyst, approaching that of the unselectivated zeolite. Thus, after air regeneration, the catalyst has required reselectivation, i.e., controlled precoking, to restore the desired initial selectivity.

SUMMARY OF THE INVENTION

In accordance with the present invention, it has been discovered that a coke selectivated catalyst comprising a crystalline aluminosilicate zeolite characterized by a silica to alumina mole ratio of at least about 12 and a constraint index within the approximate range of 1 to 12 after use in catalytic conversion of aromatic feedstock under conditions which effect undesirable deposition of a carbonaceous deposit thereon with consequent loss in activity can be regenerated in a non-oxidizing hydrogen-rich atmosphere to substantially restore activity and selectivity.

It has been found that the activity-reducing carbonaceous deposit laid down during the processing operation can be removed by exposure to an effective amount of hydrogen at elevated temperature whereby selectivity-enhancing coke deposited during controlled precoking is retained.

Hydrogen regeneration is accomplished by flowing hydrogen or a hydrogen-rich gas over the aged deactivated catalyst. Regeneration is effectively carried out at a temperature between about 800° and about 1200° F. and a pressure within the range of about 0 to about 2000 psig.

DESCRIPTION OF SPECIFIC EMBODIMENTS

Figure 1:
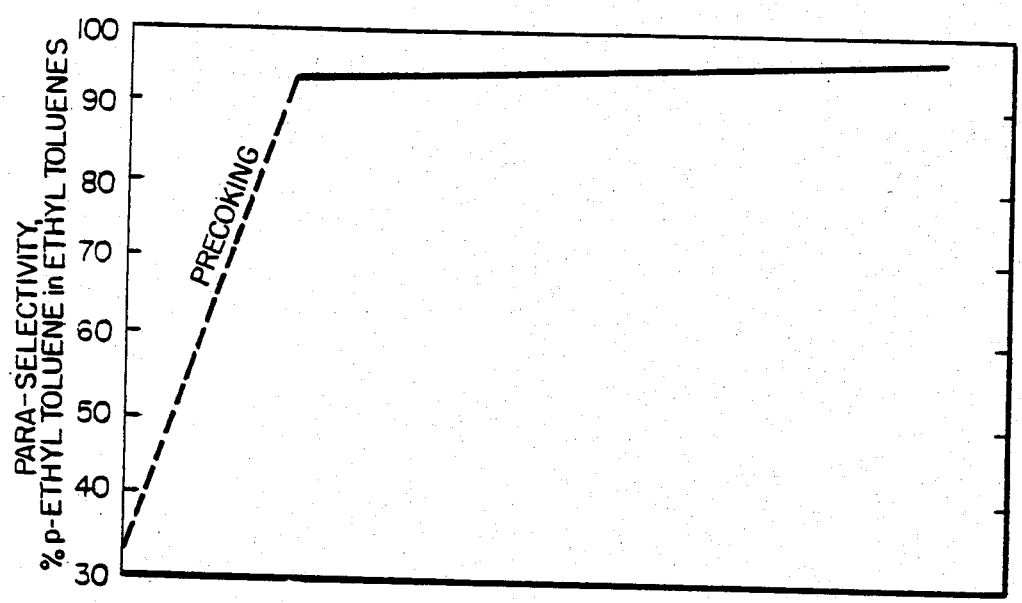
FIG. 1 of the drawing depicts selectivity for para ethyltoluene and conversion of toluene with time on stream during alkylation of toluene with ethylene over a coke-selectivated crystalline aluminosilicate zeolite catalyst of the type used in the present invention.
Figure 1:
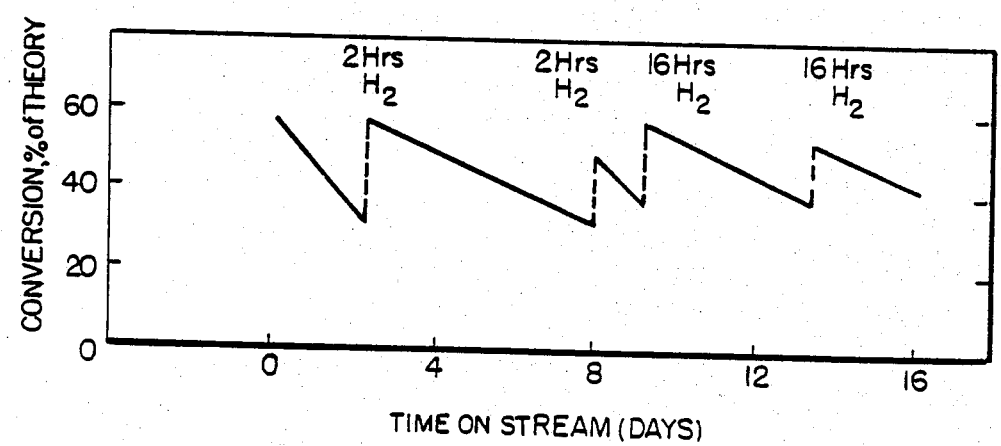

The catalyst undergoing regeneration in accordance with the method described herein comprises a crystalline aluminosilicate zeolite which is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons.

The class of zeolites defined herein is exemplified by ZSM-5, ZSM-11, ZSM-12, ZSM-35 and ZSM-38 and other similar materials. U.S. Pat. No. 3,702,886 describing ZSM-5 is incorporated herein by reference.

Suitable precoked zeolite catalysts for use in the present process comprise various ZSM-5 type materials, which are disclosed in U.S. Pat. No. 4,358,395 issued to the inventors herein on Nov. 9, 1982, the disclosure of which is incorporated herein by reference.

The crystalline aluminosilicate zeolite catalysts employed are coke selectivated prior to use by exposing the catalyst to a thermally decomposable organic compound, e.g., toluene, under high severity conditions at a temperature in excess of the decomposition temperature of said compound, generally greater than 1000° F., but less than abut 1200° F., at a hydrogen to organic compound mole ratio between 0 and 1 to deposit the desired quantity of coke thereon, generally an amount of at least about 1 percent by weight.

For toluene and organic compounds of similar reactivity, the temperature employed is greater than 1000° F. With organic compounds that are more readily decomposable than toluene, precoking can be carried out at a temperature of less than 1000° F. With the use of higher temperatures in the aforenoted range, the presence of hydrogen has not been found necessary. With temperatures of less than about 1100° F., preferably some hydrogen, generally at least 0.2 mole of hydrogen per mole of organic compound is desirable.

Organic materials, thermally decomposable under the above temperature conditions to provide coke deposition, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols, heterocyclics such as furans, thiophenes, pyrroles and pyridines. Generally, coke selectivation will be accomplished with a hydrocarbon. The reactivity of hydrocarbons with respect to coke producing decreases in the order: (1) dienes, (2) monoolefins, (3) paraffins and (4) aromatics. Usually, it is contemplated that a thermally decomposable organic compound will be used as the source of coke, which compound is the same as that subsequently undergoing conversion with the pre-coked catalyst. For example, in disproportionation of toluene, an alkyl-substituted aromatic, will be the source of coke and most preferably toluene. In the later case, toluene is initially brought into contact under conditions of temperature and hydrogen concentration amenable to rapid coke formation.

The amount of coke deposited on the catalyst, prior to conducting conversion therewith under normal process conditions, will ordinarily be at least about 1 weight percent. Generally, the amount of coke deposited will not exceed about 60 weight percent. The optimum amount of coke employed will depend among other varibles on the crystal size of the aluminosilicate zeolite used and the nature of the catalyst binder, if any, employed.

While it is contemplated that the process described herein may involve use of a crystalline aluminosilicate zeolite of any crystal size, it is preferred that the zeolite crystal size be greater than about 0.5 micron, more preferably in the approximate range of 1 to 20 microns and particularly 1 to 6 microns. It has been found that as a general rule, the smaller the zeolite crystal size the greater the amount of coke deposition required to achieve comparable results. Thus, on a binder-free basis, it has been observed that with the use of small zeolite crystals, e.g., in the range of 0.02 to 0.05 micron size, greater than 20 weight percent of coke deposition was required to obtain results comparable to those obtained with larger zeolite crystals, e.g., in the range of 1 to 2 micron, having approximately 4 weight percent of coke deposited thereon.

The amount and nature of the binder composited with the crystalline aluminosilicate zeolite also has been found to have a marked effect on the amount of coke deposition required to obtain the desired selectivity characteristics.

The regeneration method of the present invention, as aforenoted, has the advantage over the prior employed techniques wherein substantially all coke was removed from the aged catalyst by burning in an oxygen-containing atmosphere in that prior selectivation by coking is generally unnecessary.

The organic compound conversion in which the above described crystalline aluminosilicate zeolite catalysts are employed, prior to regeneration, include those reactions wherein a carbonaceous deposit is inherently laid down on the catalyst as a consequence of the conversion taking place. Typical conversion processes, given by way of example, include the alkylation of benzenoids with lower ($C_1$ to $C_3$) alkylating agents such as alkanols, as described in U.S. Pat. Nos. 3,965,207; 3,965,208; 3,965,209; and 4,002,698; disproportionation of toluene to produce benzene and xylenes rich in the para isomer described in U.S. Pat. No. 4,011,276 and 4,097,543; isomerizatin of xylenes described in U.S. Pat. No. 3,856,872; alkylation of mononuclear aromatic hydrocarbons with olefins described in U.S. Pat. Nos. 3,751,504; and 4,016,218; ethylation of toluene or ethylbenzene to selectively produce the para ethyl derivative thereof described in U.S. Pat. Nos. 4,086,287 and 4,128,592; and selective production of para dialkyl substituted benzenes described in U.S. Pat. No. 4,117,026.

In accordance with the regeneration method of the present invention, the aged catalyst resulting from use in catalyzing an organic compound conversion of the type indicated hereinabove and containing carbonaceous deposit as a result of such conversion in an amount generally between about 0.5 and about 20 weight percent, is exposed to non-oxidizing atmosphere rich in hydrogen. While the presence of inert gases, e.g., nitrogen, methane, carbon monoxide and carbon dioxide may be tolerated, it is generally preferred that the regeneration atmosphere consist essentially of hydrogen and is substantially free of oxygen or other oxidizing gas. The regeneration conditions are important to the success of the operation. Generally, a temperature between about 800° and about 1200° F. and preferably between about 900° and about 1100° F. will be employed, with the pressure advantageously being between about 100 and 1000 psig. The use of higher temperatures and pressures within the aforenoted ranges lead to faster regeneration rates.

It is of interest to note that any coke which was deposited during the selectivation procedure, to obtain a catalyst which provides higher selectivities, for example, to a para oriented product, is essentially not removed by the hydrogen regeneration treatment described herein. Without being limited by any theory, it appears that the carbonaceous deposit formed during various conversion of organic compounds such as alkylation, disproportionation, isomerization, etc. has different properties from the coke deposited during selectivation. It is believed that the carbonaceous deposit has a higher hydrogen to carbon ratio and a lower molecular weight than the coke deposited during selectivation. The latter appears to form predominately on the surface of the zeolite crystal whereas the carbonaceous deposit appears to be intracrystalline. It is the carbonaceous deposit which is selectively removed by hydrogen treatment under the conditions specified, essentially restoring the initial catalyst activity while maintaining the desired high selectivity. Such is not possible when oxygen-containing gases are used in which instance all of the coke is removed indiscriminately.

The following examples will serve to illustrate the process of the invention without limiting the same. Metric units and parts by weight are used unless otherwise indicated.

EXAMPLE 1

A sample of HZSM-5 (2.0 grams), characterized by a crystal size of 1-2 microns, in the form of extrudate with 35 weight percent alumina, was selectivated with coke. Selectivation conditions included passing a stream of toluene and hydrogen over the zeolite for 25 hours at 1100° F., 6.5 WHSV, 0.5 $H_2$/toluene and 30 psig.

EXAMPLE 2

The selectivated catalyst of Example 1 was tested for toluene disproportionation by passing a stream of toluene thereover at WHSV of 6.5, a pressure of 400 psig and a hydrogen/hydrocarbon ratio of 4 at a temperature of 900° F. At 17 percent conversion, the para-xylene content of the total xylenes produced was 75 percent.

EXAMPLE 3

The catalyst prepared in Example 1 was then tested for ethylation of toluene by contacting with a toluene/ethylene/hydrogen stream at a weight hourly space velocity of 28/1.1/0.24, a temperature of 797° F. and a pressure of 100 psig. At a toluene conversion of 55 percent of theory, there was observed 90 percent of para-ethyltoluene in the ethyltoluenes produced. Toluene conversion dropped to 30 percent after two days on stream.

EXAMPLE 4

The catalyst used in Example 3 was then regenerated by treating with hydrogen at a rate of 100 cc of hydrogen per minute for 2 hours at 1000° F. It was found that the catalyst could be restored to its initial activity and selectivity.

The catalyst then aged during the next six days to 30 percent conversion. A two hour regeneration by treatment with hydrogen under the above conditions did not completely restore the initial catalyst activity. However, increasing the regeneration time to 16 hours restored the activity as did a subsequent 16 hour regeneration. The selectivity to para-ethyltoluene gradually increased from 90 to 93 percent during the 16 days on stream and was not affected by the hydrogen regeneration.

The above results employing hydrogen regeneration are shown graphically in FIG. 1.

EXAMPLE 5

A sample of HZSM-5 (1.0 g), characterized by a crystal size of 1-2 microns, in the form of an extrudate with 35 weight percent alumina, was selectivated with coke. Selectivation conditions included passing a stream of toluene over the extrudate particles for 112 hours at 1050° F., 6.5 WHSV, 0.5 $H_2$/HC and 30 psig.

EXAMPLE 6

The selectivated catalyst of Example 5 was used for toluene disproportionation for six months by passing a stream of toluene thereover at a WHSV of 6.5, $H_2$/HC=4, and a pressure of 400 psig. During this period, catalyst aging was compensated by increasing the temperature from 900° F. at the beginning to 905° F. at the end of the cycle. The toluene conversion was 24 percent. The para-xylene content of the total xylenes produced was 82 percent at the beginning and 93 percent at the end of the six month period. For comparison, the catalyst prior to coke selectivation gave xylenes containing only 30% p-xylene.

EXAMPLE 7

The used catalyst of Example 6 was hydrogen regenerated by passing hydrogen thereover at 1000° F. and 400 psig for a total of 68 hours. After this regeneration, the catalyst produced 82 percent para-xylene in total xylenes at 24 percent conversion at a temperature of 900° F., i.e., at the test conditions at the beginning of the catalytic cycle of Example 6.

Figure 2:
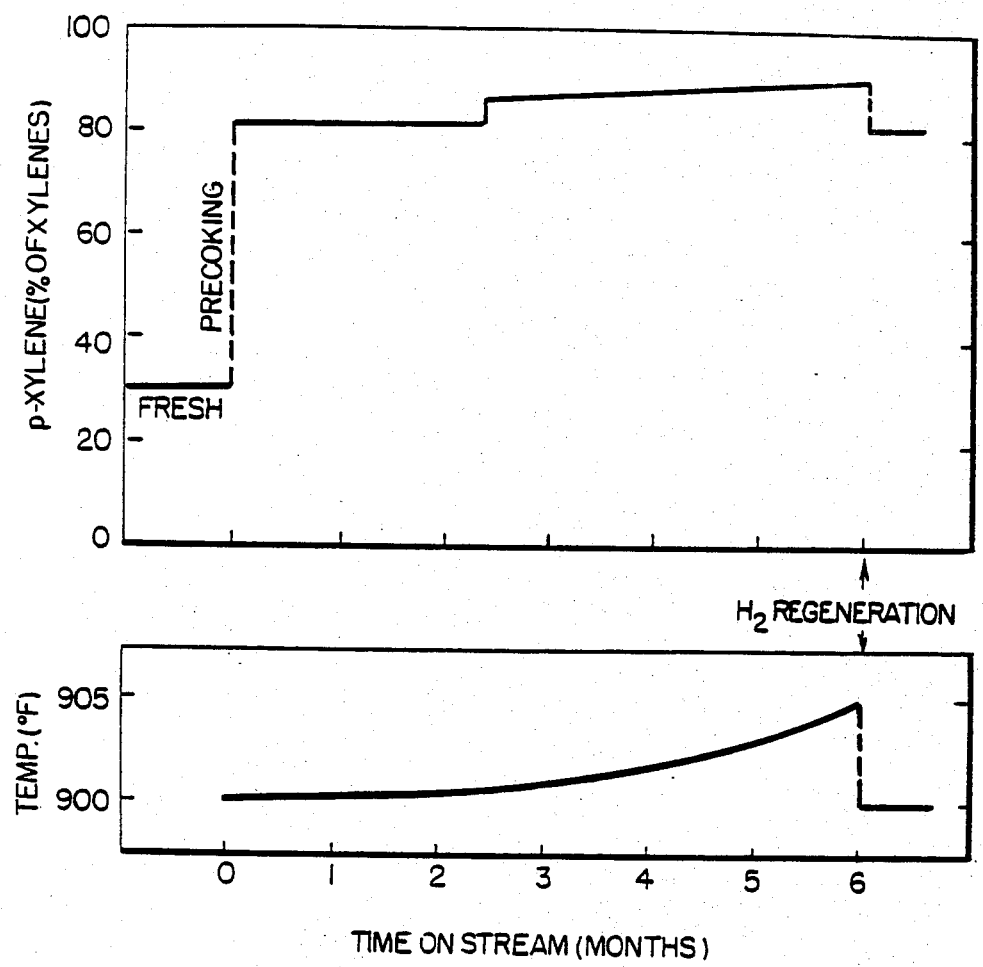
FIG. 2 of the drawing depicts selectivity for para xylene and conversion of toluene with time on stream during disproportionation of toluene over a coke-selectivated crystalline aluminosilicate zeolite catalyst of the type used in the present invention.

The para-xylene selectivity changes for the catalyst materials of Example 5, 6 and 7 are summarized in FIG. 2.

It is to be understood that the foregoing description is merely illustrative of preferred embodiments of the invention of which many variations may be made by those skilled in the art within the scope of the following claims without departing from the spirit thereof.

What is claimed is:

1. A process for catalytically converting an organic feedstock by alkylation, disproportionation and/or isomerization comprising at least one aromatic compound by contacting the feedstock under catalytic conversion conditions with a catalyst comprising a crystalline aluminosilicate zeolite characterized by a silica to alumina mole ratio of at least about 12 and a constraint index within the approximate range of 1 to 12, which catalyst has undergone controlled precoking by contact with a thermally decomposable organic compound at a temperature in excess of the decomposition temperature of said compound but less than about 1200° F. at a hydrogen to organic compound mole ratio of between 0 to 1 to deposit at least about 1 weight percent of coke thereon and using the thus precoked catalyst in conversion of said feedstock to a product comprising at least one mononuclear alkyl-aromatic compound under conditions of lesser severity which include at least one variable of a lower temperature or a higher hydrogen concentration than employed during the aforesaid precoking with consequent loss in conversion activity of said catalyst and thereafter effecting regeneration of the aged catalyst by exposure to an atmosphere comprising hydrogen at a temperature between about 800° F. and about 1200° F. and a pressure between about 0 and about 2000 psig for a period of time sufficient to at least partially restore the activity of the catalyst.

2. The method of claim 1 wherein the regenerated catalyst is further used in catalyzing aromatic feedstock conversion.

3. The method of claim 1 wherein said crystalline aluminosilicate zeolite comprises ZSM-5.

4. The method of claim 1 wherein the regeneration conditions include a temperature between about 900° and 1100° F. and a pressure between about 100 and about 1000 psig.

5. The method of claim 1 wherein said period of time is between about 1 and and about 48 hours.

6. The method of claim 1 wherein said thermally decomposable organic compound and said organic charge are the same.

7. The method of claim 1 wherein said feedstock comprises at least one alkyl aromatic compound.

8. The method of claim 1 wherein feedstock consists essentially of toluene.

9. The method of claim 1 wherein said conversion involves alkylation of an aromatic hydrocarbon.

10. The method of claim 9 wherein said alkylation involves ethylation of toluene.

11. The method of claim 1 wherein said organic compound conversion involves disproportionation of mononuclear lower alkyl aromatic hydrocarbon.

12. The method of claim 1 wherein said organic compound conversion involves isomerization of an alkyl aromatic hydrocarbon.

13. The method of claim 1 wherein said conversion comprises xylene isomerization to a para-xylene rich product.

14. In the process of converting an aromatic feedstock by alkylation, disproportionation and/or isomerization to an alkyl-substituted mono-nuclear aromatic product by contacting the feedstock with a coke-selectivated ZSM-5 type zeolite catalyst at elevated temperature under conversion conditions to produce said alkyl-substituted mononuclear aromatic product, the improvement which comprises:

regenerating the process coked catalyst in contact with a non-oxidizing atomsphere comprising an effective amount of hydrogen at elevated temperature to restore activity of the catalyst while retaining selectivity.

15. The process of claim 14 wherein the regeneration is conducted at a temperature of about 800° F. to 1200° F. and the aromatic product comprises para lower dialkyl benzene.

16. The process of claim 14 wherein the catalyst comprises HZSM-5.

17. The process of claim 16 wherein the catalyst comprises an extrudate of zeolite and alumina.

* * * * *